United States Patent
Doidge et al.

(10) Patent No.: US 10,932,725 B2
(45) Date of Patent: Mar. 2, 2021

(54) DIAGNOSIS OF MIGRAINE VIA EXPERT SYSTEM

(71) Applicant: Cerebral Diagnostics Canada Incorporated, Toronto (CA)

(72) Inventors: Mark S. Doidge, Toronto (CA); Mario Garingo, Toronto (CA); Farhang Sahba, Toronto (CA)

(73) Assignee: HEADACHE SCIENCES INCORPORATED, Toronto (CA)

( * ) Notice: Subject to any disclaimer, the term of this patent is extended or adjusted under 35 U.S.C. 154(b) by 450 days.

(21) Appl. No.: 15/904,956

(22) Filed: Feb. 26, 2018

(65) Prior Publication Data
US 2018/0242919 A1    Aug. 30, 2018

Related U.S. Application Data (60) Provisional application No. 62/463,238, filed on Feb. 24, 2017.

(51) Int. Cl.
*A61B 5/04* (2006.01)
*A61B 5/00* (2006.01)
(Continued)

(52) U.S. Cl.
CPC ............ *A61B 5/7267* (2013.01); *A61B 5/048* (2013.01); *A61B 5/04014* (2013.01);
(Continued)

(58) Field of Classification Search
CPC .. A61B 5/00; A61B 5/04; A61B 5/048; A61B 5/0482; A61B 5/04014;
(Continued)

(56) References Cited

U.S. PATENT DOCUMENTS

| 2006/0111644 A1* | 5/2006 | Guttag ................. | A61B 5/7207 600/544 |
| 2019/0246927 A1* | 8/2019 | Vayrynen ............. | A61B 5/7225 |

OTHER PUBLICATIONS

R. Bellotti, F. De Carlo, M. de Tommaso and M. Lucente, "Migraine detection through spontaneous EEG analysis," 2007 29th Annual International Conference of the IEEE Engineering in Medicine and Biology Society, Lyon, 2007, pp. 1834-1837, doi: 10.1109/IEMBS.2007.4352671. (Year: 2007).*

(Continued)

*Primary Examiner* — Eric J Messersmith
(74) *Attorney, Agent, or Firm* — Tarolli, Sundheim, Covell & Tummino LLP (57) ABSTRACT

Systems and methods are provided for identifying, monitoring, and treating migraines and migraineurs. An electroencephalogram (EEG) of a patient is obtained. The EEG comprises a plurality of EEG signals. At least two features are extracted of a network feature across at least one pair of the plurality of EEG signals in the alpha frequency band, a feature derived from a signal decomposition of at least one EEG signal, and a feature representing the power spectrum density of at least one EEG signal. The patient is classified into one of a plurality of classes, each representing one of the presence of migraine symptoms, a response to migraine treatment, a type of migraineur, a current stage of a migraine, and a likelihood that the patient is a migraineur, according to the extracted at least two features.

14 Claims, 3 Drawing Sheets

(51) Int. Cl.
| | |
|---|---|
| *A61B 5/048* | (2006.01) |
| *A61B 5/0482* | (2006.01) |
| *G06F 17/14* | (2006.01) |
| *G16H 50/20* | (2018.01) |
| *G06N 5/04* | (2006.01) |
| *G06N 20/00* | (2019.01) |

(52) U.S. Cl.
CPC .......... *A61B 5/0482* (2013.01); *A61B 5/4824* (2013.01); *A61B 5/4839* (2013.01); *G06F 17/14* (2013.01); *G16H 50/20* (2018.01); *A61B 5/726* (2013.01); *G06N 5/047* (2013.01); *G06N 20/00* (2019.01)

(58) Field of Classification Search
CPC ... A61B 5/7267; A61B 5/4839; A61B 5/4824; A61B 5/726; G06F 17/14; G06N 5/04; G06N 99/00; G06N 5/047; G06N 20/00; G16H 50/20
See application file for complete search history.

(56) References Cited

OTHER PUBLICATIONS

De Tommaso, et al., Visually evoked phase synchronization changes of alpha rhythm in migraine: Correlations with clinical features, International Journal of Psychophysiology,vol. 57, Issue 3, 2005, pp. 203-210, (Year: 2005).*

Z. Cao, L. Ko, K. Lai, S. Huang, S. Wang and C. Lin, "Classification of migraine stages based on resting-state EEG power," 2015 International Joint Conference on Neural Networks (IJCNN), Killarney, 2015, pp. 1-5 (Year: 2015).*

M. Nandish, et al., "Feature Extraction and Classification of EEG Signal Using Neural Network Based Techniques", International Journal of Engineering and Innovative Technology (IJEIT), vol. 2, Issue 4, Oct. 2012, 5pgs.

* cited by examiner

DIAGNOSIS OF MIGRAINE VIA EXPERT SYSTEM

RELATED APPLICATIONS

This application claims priority from U.S. Provisional Application No. 62/463,238, filed 24 Feb. 2017, the subject matter of which is incorporated herein by reference in its entirety.

TECHNICAL FIELD

This invention relates to diagnostic systems, and more particularly, to diagnosis of migraines via expert systems.

BACKGROUND

Migraine is a common disorder affecting both women and men. It is currently diagnosed mostly by questionnaire. EEG has been used to study it for many decades. Scientists have been searching for decades to create an objective test. The present invention fills a longtime unmet need in medical diagnostics.

SUMMARY OF THE INVENTION

In one example, a method is provided. An electroencephalogram (EEG) of a patient is obtained. The EEG comprises a plurality of EEG signals. At least two features are extracted of a network feature across at least one pair of the plurality of EEG signals, a feature derived from a signal decomposition of each of a first set of at least one of the plurality of EEG signals, and a feature representing the power spectrum density of each of a second set of at least one of the plurality of EEG signals. The patient is classified into one of a plurality of classes each representing one of the presence of migraine symptoms, a response to migraine treatment, a type of migraineur, a current stage of a migraine, and a likelihood that the patient is a migraineur, according to the extracted at least two features.

In another example, a system is provided. An electroencephalograph generates an electroencephalogram (EEG) of a patient. The EEG includes a plurality of EEG signals. A signal processor includes a feature extractor that extracts at least two features of a network feature across at least one pair of the plurality of EEG signals, a feature derived from a signal decomposition of each of a first set of at least one of the plurality of EEG signals, and a feature representing the power spectrum density of each of a second set of at least one of the plurality of EEG signals. A classifier classifies the patient into one of a plurality of classes each representing one of the presence of migraine symptoms, a response to migraine treatment, a type of migraineur, a current stage of a migraine, and a likelihood that the patient is a migraineur, according to the extracted at least two features.

In yet another example, a method is provided for identifying migraineurs. An electroencephalogram (EEG) of a patient is obtained. The EEG includes a plurality of EEG signals. Each of a first feature representing phase synchronization across at least one pair of the plurality of EEG signals in the alpha frequency band, a second feature derived from a signal decomposition of each of a first set of at least one of the plurality of EEG signals, and a third feature representing the power spectrum density of each of a second set of at least one of the plurality of EEG signal is extracted. The patient is classified into one of a migraineur class and a non-migraineur class from the extracted first, second, and third features.

BRIEF DESCRIPTION OF THE DRAWINGS

FIG. 1 illustrates a diagnostic system for determining if a patient is a migraineur in accordance with an aspect of the present invention;

FIG. 2 illustrates one example of a method for identifying migraineurs;

FIG. 3 illustrates another example of a method for identifying migraineurs; and FIG. 4 is a schematic block diagram illustrating an exemplary system of hardware components.

DETAILED DESCRIPTION

FIG. 1 illustrates a diagnostic system 10 for evaluating a patient in accordance with an aspect of the present invention. An electroencephalogram (EEG) device 12 can be used to extract EEG data from the patient. This data is provided to a signal processor 20 implemented as computer readable instructions, executed by a processor 14 and stored on a non-transitory computer readable medium 30. The signal processor 20 includes a feature extractor 32 that extracts a vector of feature values from the EEG data. Exemplary features can include various parameters representing comparisons across the various EEG signals, a signal decomposition of the EEG data, and features representing spectral power. In the illustrated example, the feature extractor 32 extracts at least two features of a network feature across at least one pair of the plurality of EEG signals, a feature derived from a signal decomposition of each of a first set of at least one of the plurality of EEG signals, and a feature representing the power spectrum density of each of a second set of at least one of the plurality of EEG signals By a network feature, it is meant a feature that describes the interaction between one or more areas of the brain, and thus for the purpose of EEG data, either comparisons of current densities at anatomical locations, determined, for example, via source localization techniques, or comparisons between signals obtained at different electrodes. To infer interaction between local areas or electrodes, thresholds and phase synchronization can be applied. In one implementation, phase synchronization can be used to represent temporal and spatial frequency abnormalities found in EEG signals taken from migraineurs. To this end, at least two EEG signals are filtered to only contain a frequency band of interest. In one implementation, this is the alpha band frequency, which is between eight and thirteen hertz. A Hilbert transform can be performed on the signal from each electrode to obtain a transformed signal, and a strong analytic signal representing each electrode output can be obtained as a sum of the original signal, $s_i$ from the electrode and the Hilbert transform of that signal such that for the $i^{th}$ electrode, the analytic signal, $S_i(t)$ can be written as:

$$S_i(t)=s_i+j\tilde{s}_i=A_i(t)e^{j\Phi(t)} \quad \text{Eq. 1}$$

wherein $A_i(t)$ is an envelope of the analytic signal for the $i^{th}$ electrode and $\Phi_i(t)$ is a phase of the analytic signal for the $i^{th}$ electrode.

A difference in the phase, $\Delta\Phi_{xy}(t)$, between the two signals from two electrodes, x and y, is defined as $\Phi_x(t)-\Phi_y(t)$. An alpha band phase synchronization feature for two electrodes, $ABS_{xy}$ can be calculated as the magnitude sum of the differences of phase between across a defined epoch, such that:

$$ABS_{xy} = \frac{1}{N}\left\|\sum_{j=1}^{N} e^{j(\Delta\Phi_{xy}(t))}\right\| \qquad \text{Eq. 2}$$

wherein N is a number of samples in the defined epoch.

While a phase synchronization feature can be calculated for each possible pair of electrodes, it will be appreciated that the potential number of features is large. In a system using thirty-two electrodes, such as a standard 10-20 arrangement, nearly five-hundred pairs will be available. Accordingly, in one implementation, the feature set can be reduced to a number of pairs most relevant to the classification. In one example, the selected set of phase synchronization features can primarily represent pairs of electrodes with at least one electrode positioned in the occipital and parietal regions. This is intended to capture increased phase synchronization in the occipital cortex, which is believed to relate to a predisposition for photophobia and future migraine attacks. In another example, a composite feature can be generated as a linear combination of the selected set of phase synchronization features, either equally weighted or weighted by a predetermined relevance of each feature. For example, the selected set of phase synchronization features can be equally weighted, and thus averaged.

The signal decomposition features can include signals derived via a Fourier transform, an Empirical Mode decomposition, a wavelet decomposition, or similar processes. In one implementation, in which a wavelet decomposition is used, the signal decomposition features include a scale-dependent and scale-invariant feature for each electrode. For a time series of voltage values from an $i^{th}$ electrode, $x_i$, the wavelet coefficients, $W_a(n)$, produced in a wavelet decomposition can be defined as:

$$W_a(n) = a^{-1}\sum_{i=1}^{M} x_i \psi\left(\frac{i-n}{a}\right) \qquad \text{Eq. 3}$$

wherein $\psi$ is the wavelet function, M is the length of the time series, and a and n define the coefficient computation locations.

A scale-dependent feature, SD, can be determined as:

$$SD = \sqrt{\frac{1}{N-1}\sum_{j=1}^{N}(W_a(n) - W_a)} \qquad \text{Eq. 4}$$

wherein N=M/a is the number of coefficients at a given scale, a, and $W_\alpha$ is a mother wavelet function.

The scale-independent feature, SI, can be calculated as the sum of the $q^{th}$ powers of the maxima of the wavelet function in Eq. 3, and represents different fractal properties of the time series of voltage values at different scaling components, $\tau(q)$, such that:

$$SI = \sum_{i} \|W_a(i)\|^2 \sim a^{\tau(q)} \qquad \text{Eq. 5}$$

It will be appreciated that the specific wavelet function, the scale, a, and the value for q can vary with the application. In one implementation, the wavelet function can be a Daubechies-12 function, a can be 3, and q can be 1.

The signal decomposition features identify abnormal transient features in the individual EEG signals to discriminate migraineurs from the normal controls. The inventors have determined that there are abnormal transient activities in the frontal and central regions of the migraineur brain as compared to non-migraineur, and the scale-dependent and scale-independent features from the electrodes in these regions can be used to represent these differences in the classification. In one example, a composite feature can be generated as a linear combination of a selected set of the scale-dependent and scale-independent features, either equally weighted or weighted by a predetermined relevance of each feature. For example, the selected set of scale-dependent and scale-independent features can be equally weighted, and thus averaged.

The autoregression features are derived via a spectral analysis model in which the voltage values of each electrode, x(n), are modelled as the output of a linear system characterized by a rational structure. A set of parameters are estimated from a given data sequence x(n), where $0 \leq n \leq N-1$, from which the power spectral density (PSD) is computed. The PSD can be computed by solving a series of linear equations whereby the data is modeled as an output of causal, all-pole, discrete filters whose input is white noise. The autoregression model for each electrode, with order p, can be expressed as:

$$x(n) = -\sum_{k=1}^{p} a(k)x(n-k) + w(n) \qquad \text{Eq. 6}$$

wherein a(k) are the p autoregression coefficients, and w(n) is a white noise signal having a variance equal to that of the signal, x(n).

In one implementation, the autocorrelation function is determined via the Burg method, with an appropriate order, p, for the autocorrelation selected according to the Akaike information criterion (AIC). Rather than using the entire spectrum as a feature, six different types of features can be extracted from each of the five main frequency ranges used in EEG analysis, alpha, beta, gamma, delta, and theta. The features can include: 1) a mean power of each frequency range; 2) a variance power of each frequency range; 3) a mean frequency of the observed mean power in each frequency range; 4) a variance frequency of the observed mean power in each frequency range, and the ratio between; 5) a mean power for each frequency range; and 6) a variance for each frequency range. It will be appreciated, however, that other descriptive statistics representing the frequency content of the signal can also be utilized.

The most discriminant features for the autoregression features are taken from the gamma, delta, and alpha ranges from electrodes in the temporal, central and parietal regions. It is believed that these features track the abnormal alpha rhythms and increased delta and gamma power associated with migraineurs. Accordingly, the autoregression features can be drawn from these ranges. In one example, a composite feature can be generated as a linear combination of a selected set of the spectral power features, either equally weighted or weighted by a predetermined relevance of each feature. For example, the selected set of spectral power features can be equally weighted, and thus averaged to provide a single feature representing the autocorrelation features.

In another implementation, the classification features can be a change in two or more of the features described above between a first EEG, taken at a first time, and a second EEG, taken at a second time. This allows for monitoring of a patient's response to treatment.

Figure 1:
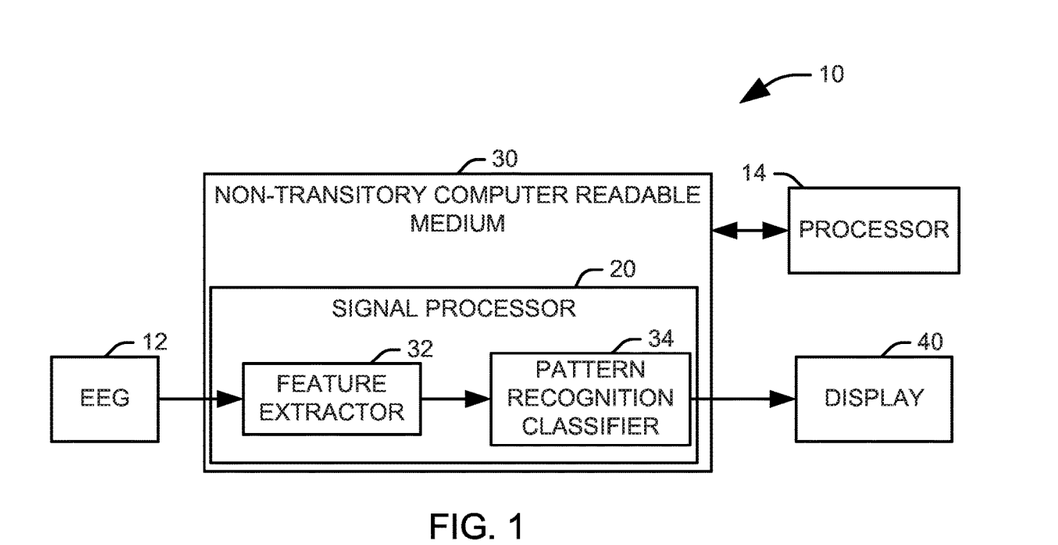

A pattern recognition classifier 34 uses the plurality of extracted features to classify a patient into one of a plurality of classes, each representing one of the presence of migraine symptoms, a response to migraine treatment, a type of migraineur, a current stage of a migraine, and a likelihood that the patient is a migraineur, according to the extracted at least two features. In one implementation, the classification is binary, with "migraineur" and "non-migraineur" classes, although it will be appreciated that additional classes could be included, for example, classes representing likelihoods that the patient is a migraineur or classes representing types of migraines or migraineurs, such as "migraine with aura" and "migraine without aura" classes. In another implementation, the classes could represent various stages of a migraine. In yet another implementation, the classes could represent a patient's response to treatment, for example, "improving", "no change", and "degrading" classes, or classes representing degrees of response to treatment.

The pattern recognition classifier 34 can utilize one or more pattern recognition algorithms, each of which analyze the extracted features or a subset of the extracted features to classify the patients into one of the plurality of classes and provide this information to a display 40. Where multiple classification algorithms are used, an arbitration element can be utilized to provide a coherent result from the plurality of classifiers. Each classifier is trained on a plurality of training samples representing the classes of interest. The training process of the a given classifier will vary with its implementation, but the training generally involves a statistical aggregation of training data from a plurality of training samples into one or more parameters associated with the output class. Any of a variety of optimization techniques can be utilized for the classification algorithm, including support vector machines, self-organized maps, linear discriminant analysis, fuzzy logic systems, data fusion processes, ensemble methods, rule-based systems, or artificial neural networks.

For example, a support vector machine (SVM) classifier can process the training data to produce functions representing boundaries in a feature space defined by the various features. Similarly, an artificial neural network (ANN) classifier can process the training data to determine a set of interconnection weights corresponding to the interconnections between nodes in the neural network.

An SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. A rule-based classifier applies a set of logical rules to the extracted features to select an output class. Generally, the rules are applied in order, with the logical result at each step influencing the analysis at later steps. A regression model can be configured to calculate a parameter representing a likelihood that a patient is a migraine sufferer based on a set of predetermined weights applied to the elements of the feature vector.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier. In a binary classification, the final layer of nodes can include only a single node, which can be translated to a confidence value that a patient is a migraine sufferer.

Figure 2:
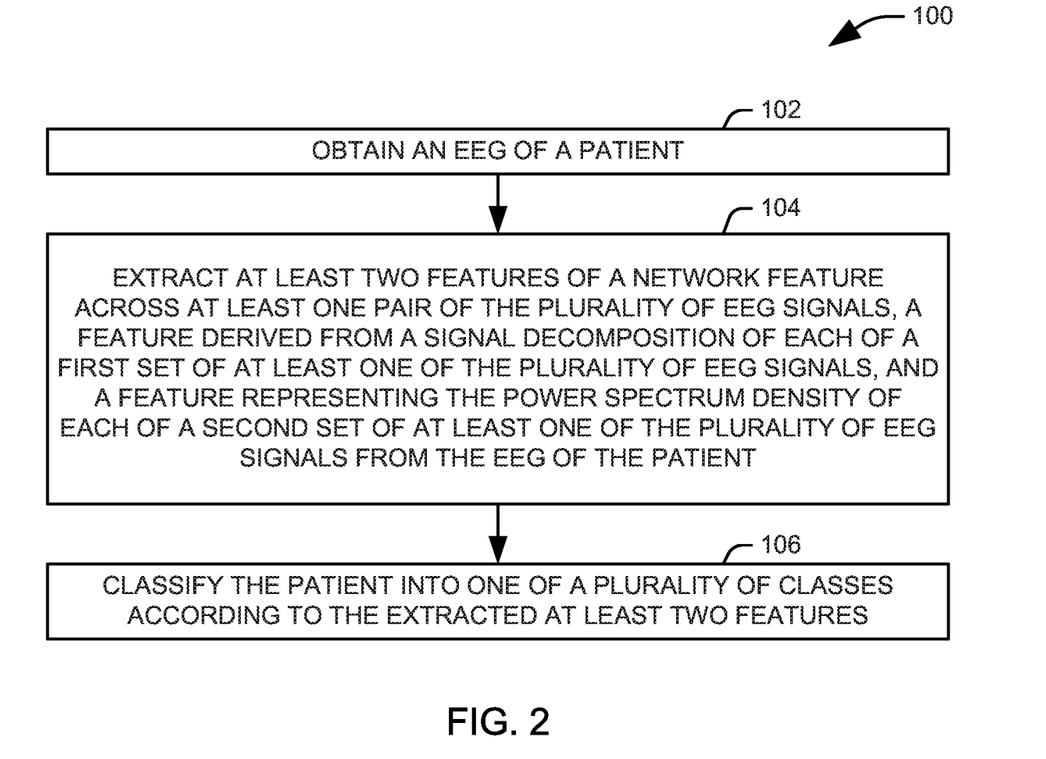
Figure 3:
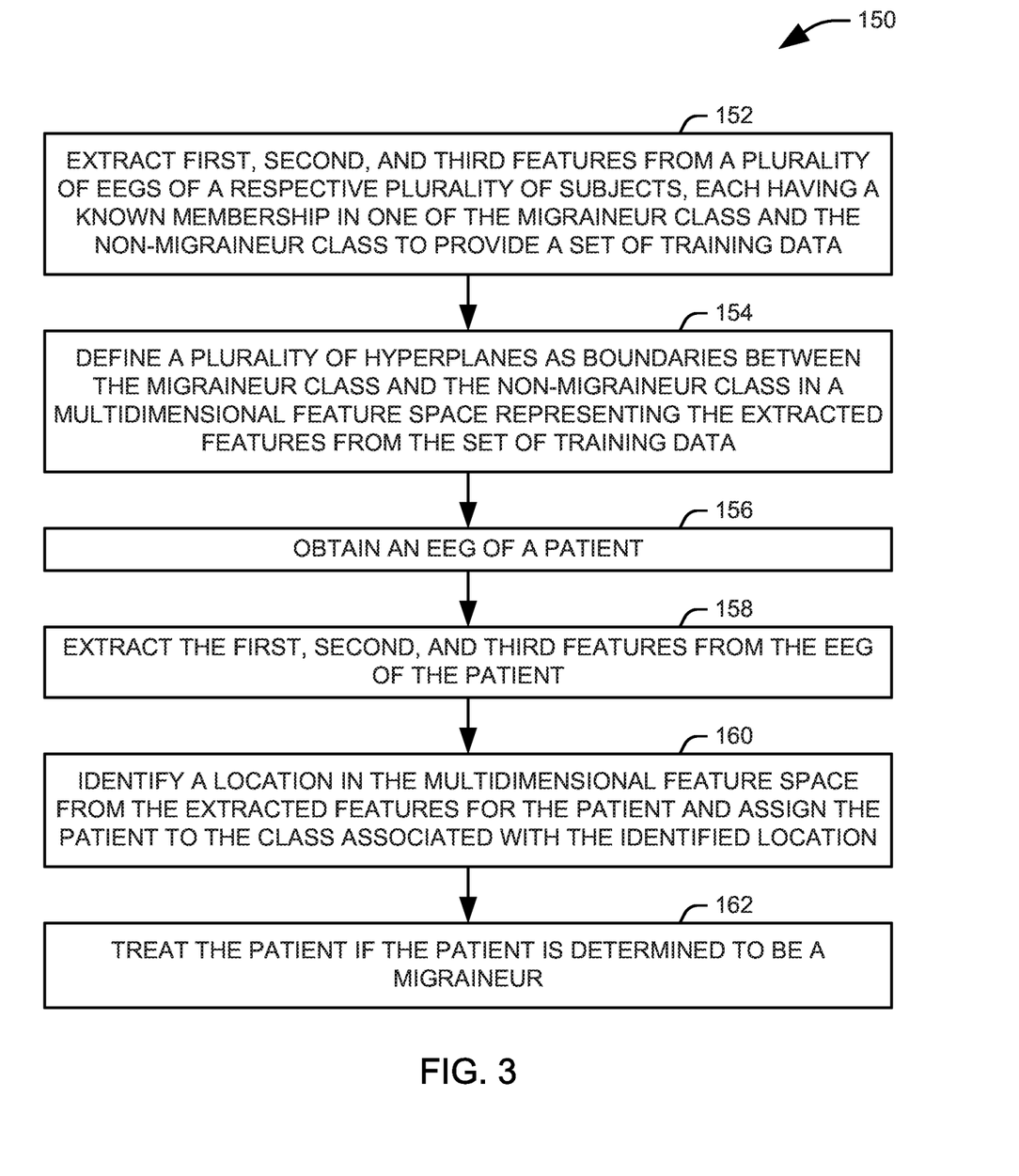

In view of the foregoing structural and functional features described above, example methods will be better appreciated with reference to FIGS. 2 and 3. While, for purposes of simplicity of explanation, the example methods of FIGS. 2 and 3 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

FIG. 2 illustrates one example of a method 100 for identifying migraineurs. At 102, an electroencephalogram (EEG) of a patient is obtained. The EEG includes a plurality of EEG signals, each taken from an electrode placed on the scalp of the patient. At 104, at least two features are extracted from a network feature across at least one pair of the plurality of EEG signals, a feature derived from a signal decomposition of each of a first set of at least one of the plurality of EEG signals, and a feature representing the power spectrum density of each of a second set of at least one of the plurality of EEG signals. In one implementation, features of all three types are extracted.

In one implementation, phase synchronization features are extracted from one or more frequency bands. Each EEG signal of the at least one pair of EEG signals is filtered to provide only the desired frequency bands to provide respective filtered signals, and a Hilbert transform is applied to each filtered signal to provide respective analytic signals. The analytic signals for a given pair of the at least one pair of EEG signals within each frequency band are compared to provide a phase difference between the given pair, and the phase difference between the given pair is summed over a period of time. In one implementation, not all pairs of EEG signals are evaluated, and most or all of the pairs of EEG signals include signals taken from the occipital and parietal regions.

In one implementation using signal decomposition features, one implementation a set of coefficients are extracted for each of the at least one EEG signal from a wavelet decomposition and a scale-dependent feature and a scale-independent feature is derived for each of the first set of at least one EEG signal from the generated set of wavelet coefficients. In one implementation, the wavelet decomposition uses a Daubechies-12 wavelet function with a scale of three, although it will be appreciated that other wavelet functions and scales can be utilized. In one implementation, not all EEG signals are evaluated, and most or all of the EEG signals include signals taken from the frontal and central regions.

Where features representing the power spectrum density are extracted, each of the second set of at least one EEG signal is divided into a plurality of frequency bands, a set of autoregression coefficients is calculated for each of the plurality of frequency bands, and for each frequency range, and at least one descriptive statistic is determined representing the signal power. In one implementation, the frequency bands of interest are the alpha, delta, and gamma frequency bands.

At 106, the patient is classified into one of a plurality of classes according to the extracted at least two features. In one implementation, the patient is classified via a support vector machine trained on known training samples taken from patients whose associated class is known. In one example, each of a set of multiple phase synchronization features in the alpha frequency band, a set of multiple signal decomposition features, and a set of multiple features representing the power spectrum density are extracted. Each set of features can be further decomposed to extract only meaningful features for classification. Appropriate methods for feature decomposition can include Lasso, ElasticNet, Randomized PCA, ISO MAP, SPECTRAL Embedding, Random Projections, Tree Based Methods, Recursive Feature Selection, and Multivariate feature reduction. These features can be combined as a linear combination with weighted terms to form a composite feature, which can then be used for classification. This reduces the complexity of the classifier and reduces the likelihood of overfitting the classifier to the known training samples. It will be appreciated, If the patient is determined to be a migraineur, treatment can be provided, such as behavioral biofeedback, training in relaxation techniques, and pharmaceutical interventions.

FIG. 3 illustrates another example of a method 150 for identifying migraineurs. At 152, first, second, and third features are extracted from a plurality of electroencephalograms (EEGs) of a respective plurality of subjects, each having a known membership in one of the migraineur class and the non-migraineur class to provide a set of training data. Each EEG comprises a plurality of EEG signals, taken from the various electrodes affixed to the subject's scalp. The first feature represents phase synchronization across at least one pair of the plurality of EEG signals in the alpha frequency band, the second feature is derived from a signal decomposition of each of a first set of at least one of the plurality of EEG signals, and the third feature represents the power spectrum density of each of a second set of at least one of the plurality of EEG signals. For consistency, this data can be taken from the subjects when no migraine symptoms are present.

At 154, at least one hyperplane is defined as a boundary between the migraineur class and the non-migraineur class in a multidimensional feature space representing the extracted first, second, and third features from the set of training data. In accordance with an aspect of the present invention, the hyperplanes can be defined to divide the training samples within the feature space according to their respective classes while maximizing the distance between the boundaries and any training sample. It will be appreciated that the training sets may not always be linearly separable in the feature space defined by the extracted features, and that the original feature space can be mapped into a higher-dimensional space via an appropriate kernel to facilitate definition of the hyperplane boundaries.

At 156, an EEG of a patient is obtained. At 158, the first, second, and third features are extracted from the EEG of the patient. At 160, the patient is classified into one of a migraineur class and a non-migraineur class by identifying a location in the multidimensional feature space from the extracted first, second, and third features for the patient and assigning the patient to the class associated with the identified location. At 162, the patient is provided with treatment. Appropriate treatments can include one of biofeedback, training in relaxation techniques, psychotherapy, cognitive behavioral therapy, training in mindfulness, sleep treatments, and a pharmaceutical intervention if the patient is determined to be a migraineur.

Figure 4:
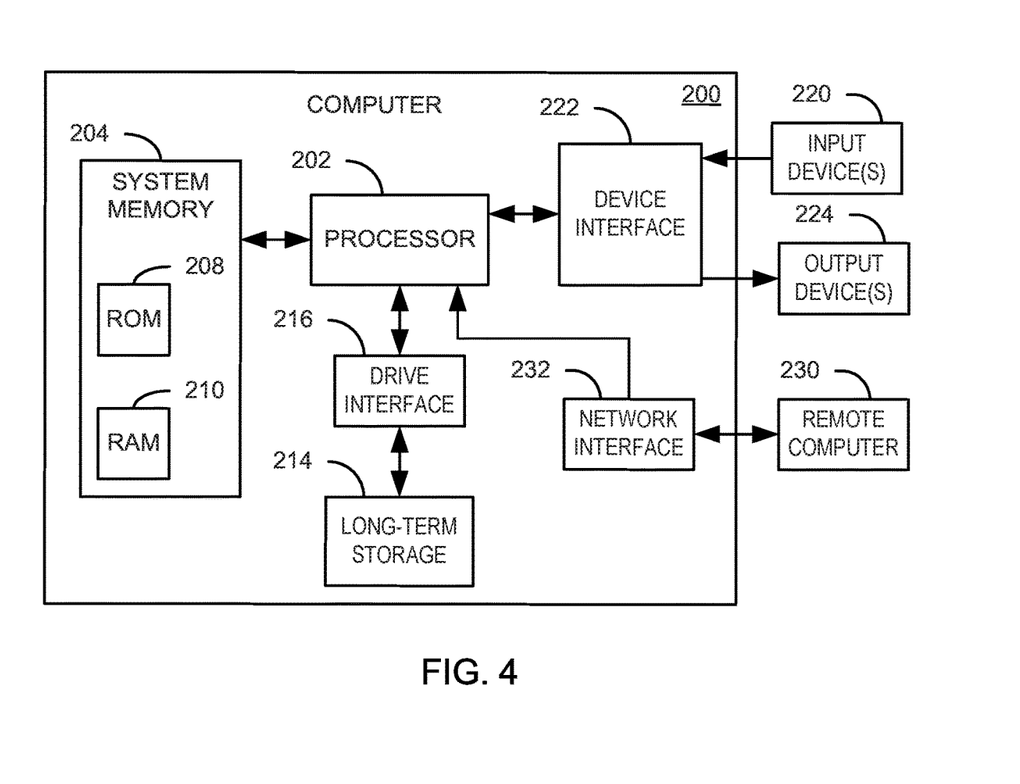

FIG. 4 is a schematic block diagram illustrating an exemplary system 200 of hardware components capable of implementing examples of the systems and methods disclosed herein. The system 200 can include various systems and subsystems. The system 200 can be a personal computer, a laptop computer, a workstation, a computer system, an appliance, an application-specific integrated circuit (ASIC), a server, a server BladeCenter, a server farm, etc.

The system 200 can include a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard, touch screen, and/or a mouse). The system bus 202 can be in communication with the processing unit 204 and the system memory 206. The additional memory devices 208 and 210, such as a hard disk drive, server, standalone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208, and 210 can store data, programs, instructions, database queries in text or compiled form, and any other information that may be needed to operate a computer. The memories 206, 208 and 210 can be implemented as computer-readable media (integrated or removable), such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a diagnostic system in accordance with the present invention, in particular, the feature extractor 22 and the pattern recognition classifier 32. Computer executable logic for implementing the diagnostic system resides on one or more of the system memory 206, and the memory devices 208 and 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution. This medium may be distributed across multiple discrete assemblies all operatively connected to a common processor or set of related processors.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
    obtaining an electroencephalogram (EEG) of a patient, the EEG comprising a plurality of EEG signals, each of the plurality of EEG signals representing an output of an associated electrode of a plurality of electrodes associated with an EEG device;
    extracting at least two features of:
    1. a network feature across at least one pair of the plurality of EEG signals;
    2. a feature derived from a signal decomposition one of the plurality of EEG signals; and
    3. a feature representing the power spectrum density one of the plurality of EEG signals; and
    classifying the patient into one of a plurality of classes, each class of the plurality of classes representing one of the presence of migraine symptoms, a response to migraine treatment, a type of migraineur, a current stage of a migraine, and a likelihood that the patient is a migraineur, according to the extracted at least two features.

2. The method of claim 1, further comprising treating the patient with one of biofeedback, training in relaxation techniques, psychotherapy, cognitive behavioral therapy, training in mindfulness, sleep treatments, and a pharmaceutical intervention.

3. The method of claim 1, wherein extracting the at least two features comprises extracting the network feature across at least one pair of the plurality of EEG signals and extracting the network feature across at least one pair of the plurality of EEG signals comprises extracting a representing phase synchronization across at least one pair of EEG signals in a frequency band of interest.

4. The method of claim 3, wherein representing phase synchronization across two EEG signals in the frequency band of interest comprises:
    filtering each EEG signal of the a given pair of the at least one pair of EEG signals such that all frequencies other than the frequency band of interest are suppressed to provide respective filtered signals;
    applying a Hilbert transform to each filtered signal to provide respective analytic signals;
    comparing the analytic signals for the given pair of EEG signals to provide a phase difference between the given pair of EEG signals; and
    summing the phase difference between the given pair of EEG signals over a period of time.

5. The method of claim 3, wherein the at least one pair of EEG signals comprises a plurality of pairs of EEG signals and the method further comprises averaging the summed phase difference for each of the plurality of pairs of signals to provide a single feature representing phase synchronization in the alpha frequency band.

6. The method of claim 3, wherein the frequency band of interest is the alpha band.

7. The method of claim 3, wherein an EEG signal of each of the at least one pair of EEG signals is taken from an electrode in one of the occipital and parietal regions.

8. The method of claim 1, wherein extracting the at least two features comprises extracting the feature derived from the signal decomposition of each of the first set of at least one EEG signal, and extracting the feature derived from the signal decomposition of each of the first set of at least one EEG signal comprises generating a set of coefficients for each of the at least one EEG signal from a signal decomposition and deriving a scale-dependent feature for each of the first set of at least one EEG signal from the generated set of coefficients.

9. The method of claim 8, wherein the signal decomposition is a wavelet decomposition.

10. The method of claim 8, wherein each EEG signal of first set of EEG signals is taken from an electrode in one of the frontal and central regions.

11. The method of claim 1, wherein extracting at least two features comprises extracting the feature representing the power spectrum density of each of the second set of at least one EEG signal and extracting the feature representing the power spectrum density of each of the second set of at least one EEG signal comprises dividing each of the second set of at least one EEG signal into a plurality of frequency bands, calculating a set of autoregression coefficients for each of a selected set of the plurality of frequency bands, and determining, for each frequency band in the selected set, at least one descriptive statistic representing the signal power.

12. The method of claim 1, wherein extracting the at least two features comprises extracting each of the feature representing phase synchronization across at least one pair of the plurality of EEG signals in the alpha frequency band, the feature derived from the signal decomposition of each of the first set of at least one EEG signal, and the feature representing the power spectrum density of each of the second set of at least one EEG signal.

13. The method of claim 1, further comprising:
    extracting the at least two features from a plurality of electroencephalograms (EEGs) of a respective plurality of subjects each having a known membership in one of the plurality of classes to provide a set of training data; and
    defining at least one hyperplane defining a boundary between the plurality of classes in a multidimensional feature space representing the extracted the at least two features from the set of training data such that a distance between the at least one hyperplane and a nearest sample in the set of training data is maximized;
    wherein classifying the patient into one of a plurality of classes according to the extracted at least two features comprises identifying a location in the multidimensional feature space from the extracted at least two features for the patient and assigning the patient to a class of the plurality of classes associated with the identified location.

14. The method of claim 1, wherein obtaining the EEG of a patient comprises obtaining a first EEG of the patient at a first time, the method further comprising obtaining a second EEG of the patient at a second time, and extracting the at least two features comprising extracting at least two of a difference in the network feature across the at least one pair of the plurality of EEG signals between the first time and the second time, a difference in the feature derived from a signal decomposition of each of the first set of EEG signals between the first time and the second time, and a difference in the feature representing the power spectrum density of each of the second set of EEG signals between the first time and the second time.

* * * * *